United States Patent
Strand et al.

(10) Patent No.: US 8,906,347 B2
(45) Date of Patent: Dec. 9, 2014

(54) ORAL STANNOUS COMPOSITIONS

(75) Inventors: Ross Strand, Bracknell (GB); Maurice Joseph Prendergast, Bracknell (GB); Xiaoli Wang, Beijing (CN)

(73) Assignee: The Procter & Gamble Co., Cincinnati, OH (US)

( * ) Notice: Subject to any disclaimer, the term of this patent is extended or adjusted under 35 U.S.C. 154(b) by 1364 days.

(21) Appl. No.: 12/266,937

(22) Filed: Nov. 7, 2008

(65) Prior Publication Data
US 2009/0136432 A1    May 28, 2009

(30) Foreign Application Priority Data

Nov. 9, 2007 (EP) .................................... 07120425

(51) Int. Cl.
| | | |
|---|---|---|
| *A61Q 11/00* | (2006.01) | |
| *A61K 8/00* | (2006.01) | |
| *A61K 8/21* | (2006.01) | |
| *A61K 8/27* | (2006.01) | |
| *A61K 8/25* | (2006.01) | |
| *A61K 8/73* | (2006.01) | |
| *A61K 8/19* | (2006.01) | |
| *A61K 8/55* | (2006.01) | |
| *A61K 8/24* | (2006.01) | |

(52) U.S. Cl.
CPC . *A61Q 11/00* (2013.01); *A61K 8/73* (2013.01); *A61K 8/25* (2013.01); *A61K 8/19* (2013.01); *A61K 8/55* (2013.01); *A61K 8/24* (2013.01); *A61K 8/21* (2013.01); *A61K 8/27* (2013.01)
USPC ................................ 424/49; 424/52; 424/401

(58) Field of Classification Search
USPC ............................................ 424/49, 52, 401
See application file for complete search history.

(56) References Cited

U.S. PATENT DOCUMENTS

| | | | |
|---|---|---|---|
| 3,282,792 A | | 11/1966 | Fiscella |
| 4,335,102 A | * | 6/1982 | Nakashima et al. ............ 424/52 |
| 5,004,597 A | | 4/1991 | Majeti |
| 5,213,790 A | | 5/1993 | Lukacovic |
| 6,555,094 B1 | | 4/2003 | Glandorf |
| 2003/0206874 A1 | | 11/2003 | Doyle |
| 2007/0025928 A1 | | 2/2007 | Glandorf |
| 2007/0237726 A1 | | 10/2007 | White |

FOREIGN PATENT DOCUMENTS

| | | |
|---|---|---|
| EP | 426213 | 11/1993 |
| WO | WO 94/14406 | 7/1994 |
| WO | WO 94/14407 | 7/1994 |
| WO | WO 96/17587 | 6/1996 |
| WO | WO 00/61092 | 10/2000 |
| WO | WO 03/045344 | 6/2003 |
| WO | WO 2007/076001 | 7/2007 |

OTHER PUBLICATIONS

International Search Report and Written Opinion, Int'l Application No. PCT/IB2008/054595, date of mailing Jun. 17, 2009.
Extended European Search Report, Application No. 08168355.9-2108, dated Mar. 27, 2009.

* cited by examiner

*Primary Examiner* — Lezah Roberts
(74) *Attorney, Agent, or Firm* — James E. Oehlenschlager

(57) ABSTRACT

The present invention relates to an aqueous oral composition comprising:
a) from 0.2% to 3% divalent metal ions comprising:
  i. from 0.1% to 1.5% of zinc ions;
  ii. from 0.1% to 2% of tin (II) ions; and
b) a source of fluoride ions;
c) a silica dental abrasive;
d) one or more chelants having a MW of less than 1000 and capable of forming water-soluble complexes with the zinc ions, wherein the chelants comprise less than 0.2% linear polyphosphates having a chain length of four or more;
e) an orally acceptable carrier comprising at least 20% total water;
wherein the pH of the composition is from 5 to 6.5, the molar ratio of the chelants to the divalent metal ions is at least 0.70:1 and at least 80% by weight of the total zinc ions are solubilised within the composition.
The composition of the invention has been found to give improved antimicrobial activity from the zinc/stannous combination without significant taste, staining or stability problems, compared to compositions having lower levels of chelants.

18 Claims, No Drawings

ORAL STANNOUS COMPOSITIONS

FIELD OF THE INVENTION

The present invention relates to oral compositions comprising both tin(II) and zinc ions.

BACKGROUND OF THE INVENTION

Tin(II) (stannous) ions, provided in oral compositions by stannous fluoride and/or other stannous salts, have long been valued for the multiple benefits that they can afford, including antimicrobial effects, control of breath malodor, control of dental plaque growth and metabolism, reduced gingivitis, decreased progression to periodontal disease, reductions in dentinal hypersensitivity, and reduced coronal and root dental caries and erosion. Along with the benefits however there are some notorious problems. One of the most notable side effects of regular use of stannous fluoride is yellow-brown tooth staining. This stain is derived from pellicle, plaque and dietary component reactions with available stannous deposited on tooth surfaces during treatment with effective stannous fluoride formulations. A second side effect routinely encountered during use of effective stannous fluoride formulations is unacceptable formulation astringency. Furthermore, formulating stannous ions stably also presents a challenge as the tin(II) ion is both prone to oxidation towards tin(IV) and to precipitate from aqueous solution as stannous hydroxide. The latter is a pH dependent phenomenon and is typically avoided by formulating at a low pH and/or by formulating in an anhydrous composition. Formulating at a low pH is not preferred when a fluoride source is utilised in the presence of a silica dental abrasive however because it increases the tendency of the fluoride to react with the silica. Formulating in aqueous compositions though is of advantage for reasons, such as cost and formulation flexibility. Another approach to stabilising stannous is to include a chelating agent in the composition as disclosed e.g., in U.S. Pat. No. 3,282,792, WO 96/17587, U.S. Pat. Nos. 5,004,597, 5,213,790 and US 2007/0025928.

Zinc ions are also advantageously included in oral compositions. Combining zinc ions with stannous ions can give a broader spectrum of anti-microbial activity but zinc ions also pose increased formulation challenges through competing with the chelating agents used to stabilise stannous. The astringency of zinc is also well known and it has been found that the degree of astringency depends upon the form in which zinc is present in the composition. EP 426 213 discloses oral compositions comprising the combination of zinc and stannous as an anti-plaque system.

WO 94/14406 and WO 94/14407 describe formulating a source of zinc ions, preferably zinc oxide or zinc nitrate, along with sources of citrate and pyrophosphate ions in defined ratios. WO 00/61092 discloses increasing the bioavailability of zinc in a dentifrice by buffering the dentifrice at a pH of from 3 to 5.5. Its zinc is provided by slightly soluble zinc compounds, especially zinc citrate.

WO 2007/076001 discloses oral care compositions comprising an essentially water-insoluble zinc compound and phytate. Some of its example compositions include stannous ions.

Despite all of the foregoing, further improvements are needed in the formulation of zinc into oral compositions, in order to deliver the combination of anti-plaque efficacy with acceptable taste.

It has now been found that, by careful choice of chelant levels, oral compositions comprising fluoride, zinc and stannous can be formulated at a higher pH than has typically been used, without compromising on stannous stability. This provides advantages in fluoride stability and has also been found to avoid taste problems from the zinc.

SUMMARY OF THE INVENTION

The present invention relates to an aqueous oral composition comprising:
a) from 0.2% to 3% divalent metal ions comprising:
  (i) from 0.1% to 1.5% of zinc ions;
  (ii) from 0.1% to 2% of tin (II) ions; and
b) a source of fluoride ions;
c) a silica dental abrasive;
d) one or more chelants having a MW of less than 1000, wherein the chelants comprise less than 0.2% linear polyphosphates having a chain length of four or more;
e) an orally acceptable carrier comprising at least 20% total water;
wherein the pH of the composition is from 5 to 6.5, the molar ratio of the chelants to the divalent metal ions is at least 0.70:1 and at least 80% by weight of the total zinc ions are solubilised within the composition.

If orthophosphate ions are present, the molar ratio of orthophosphate ions to zinc ions is less than 0.2:1.

The composition of the invention has been found to give improved antimicrobial activity from the zinc/stannous combination without significant taste, staining or stability problems, compared to compositions having lower levels of chelants.

DETAILED DESCRIPTION OF THE INVENTION

Unless specified otherwise, all percentages and ratios herein are by weight of the total composition and all measurements are made at 25° C.

The present invention relates to an aqueous oral composition. The composition can be in the form of a mouth spray, mouthwash or a toothpaste or gel. Preferably the composition is in the form of a toothpaste or tooth gel suitable for use in brushing teeth.

The oral composition of the present invention includes from 0.2% to 3%, preferably from 0.3% to 2%, more preferably from 0.4% to 1.5% divalent metal ions including both zinc and tin(II) ions. Other divalent metal ions are not excluded and may include e.g. copper(II) but preferably the at least 80%, more preferably at least 90% of the divalent metal ions are stannous and zinc ions. Preferably the molar ratio of stannous ions to zinc ions is from 0.2:1 to 3:1, more preferably from 0.5:1 to 3:1, and even more preferably from 1:1 to 2:1.

Zinc Ions

A first ingredient of the oral composition herein is a source of zinc ions sufficient to provide from 0.1 to 1.5%, preferably from 0.1 to 1%, more preferably from 0.15 to 0.5% zinc ions by weight of the composition. It is an advantage of the present invention that the zinc ions are made readily bioavailable by being substantially solubilised within the composition. It is not necessary however that the source of zinc ions added to the composition should itself be water soluble since some chelating agents, such as citric acid, have the capacity to solubilise the zinc when the composition is prepared. Thus insoluble or sparingly soluble zinc compounds, such as zinc oxide or zinc carbonate, can be used as the zinc source. Preferred zinc sources however are soluble zinc sources such as zinc chloride or zinc sulphate. More preferred zinc sources are those where the zinc is already combined with a suitable chelating agent in the form of a salt or other complex, such as zinc citrate, zinc gluconate, zinc lactate and zinc glycinate. Especially preferred sources of zinc ions are zinc citrate, zinc gluconate, zinc lactate and mixtures thereof.

Stannous Ions

A second ingredient of the present oral composition is a source of stannous ions sufficient to provide from 0.1 to 2%, preferably from 0.1 to 1%, more preferably from 0.2 to 0.7% stannous (tin(II)) ions by weight of the composition. As with the zinc ions, it is an advantage of the present invention that though the stannous ions are made readily bioavailable by being substantially solubilised within the composition, the starting source of stannous ions is not critical. Suitable stannous sources include stannous fluoride, stannous chloride, stannous acetate, stannous gluconate, stannous oxalate, stannous sulfate, stannous lactate and stannous tartrate. Especially preferred sources of tin (II) ions are stannous chloride, stannous fluoride, stannous gluconate and mixtures thereof.

Fluoride Ions

A highly preferred ingredient herein is a source of fluoride ions. It is common to have a water-soluble fluoride compound present in dentifrices and other oral compositions in an amount sufficient to give a fluoride ion concentration sufficient to provide anticaries effectiveness. The oral composition herein preferably comprises a fluoride ion source sufficient to provide from 0.01% to 0.35% (100 to 3500 ppm), preferably from 0.03% to 0.2% (300 to 2000 ppm) fluoride ion. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al. Representative fluoride ion sources include: stannous fluoride, sodium fluoride, potassium fluoride, sodium monofluorophosphate, indium fluoride and many others. It has however been found that sodium monofluorophosphate can react with zinc ions to generate insoluble salts. Preferably then, the fluoride ion source comprises less than 0.2%, preferably less than 0.1 sodium monofluorophosphate. Preferred sources of fluoride ion are stannous fluoride and sodium fluoride, as well as mixtures thereof.

Abrasive

Dental abrasives are useful in oral compositions such as tooth pastes and gels for their ability to remove surface stain and pellicle and for polishing the teeth. A dental abrasive is a highly preferred ingredient of the present composition. Dental abrasives useful in the present oral composition of the subject invention include many different materials. The material selected must be one which is compatible with the composition of interest and does not excessively abrade dentin. Suitable abrasives include, for example, silicas including gels and precipitates, insoluble sodium polymetaphosphate, hydrated alumina, and resinous abrasive materials such as particulate condensation products of urea and formaldehyde. Another class of abrasives for use in the present compositions is particulate thermo-setting polymerized resins, as described in U.S. Pat. No. 3,070,510. Suitable resins include, for example, melamines, phenolics, ureas, melamine-ureas, melamine-formaldehydes, urea-formaldehyde, melamine-urea-formaldehydes, cross-linked epoxides, and cross-linked polyesters.

Silica dental abrasives of various types are preferred herein because of their unique benefits of exceptional dental cleaning and polishing performance without unduly abrading tooth enamel or dentine. Silica abrasive polishing materials herein, as well as other abrasives, generally have an average particle size ranging from 0.1 to 30 µm, and preferably from 5 to 15 µm. The abrasive can be precipitated silica or silica gels such as the silica xerogels described in U.S. Pat. Nos. 3,538,230 and 3,862,307. Examples include the silica xerogels marketed under the trade name "Syloid" by the W.R. Grace & Company, Davison Chemical Division and precipitated silica materials such as those marketed by the J. M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present invention are described in more detail in U.S. Pat. Nos. 4,340,583, 5,603,920, 5,589,160, 5,658,553, 5,651,958 and 6,740,311.

Mixtures of abrasives can be used, such as mixtures of the various grades of Zeodent® silica abrasives listed above. The total amount of abrasive in dentifrice compositions of the present invention typically ranges from 6% to 50% by weight of the composition. Dental solution, mouth spray, mouthwash and non-abrasive gel compositions of the subject invention typically contain little or no abrasive.

Chelants

The oral composition of the invention comprises one or more chelants, also known as chelating agents, having a molecular weight (MW) of less than 1000. The term "chelant", as used herein means a bi- or multidentate ligand having at least two groups capable of binding to the divalent metal ions and which, at least as part of a chelant mixture, is capable of solubilising at least 80%, preferably at least 90% of the total zinc ions within the oral composition. As much as 100% can be solubilised. Typically, those chelants useful herein will also form water soluble complexes with the stannous ions. Phytate is an exception; zinc phytate is soluble whereas stannous phytate is not. For the purpose of the present invention, the relevant molecular weight to be used for determining whether the MW is less than 1000 is that of the material added when preparing the composition e.g., if the chelant is a citrate species, which can be supplied as citric acid, sodium citrate or indeed other salt forms, the MW used is that of the particular salt or acid added to the composition but ignoring any water of crystallisation that may be present. Where necessary, e.g., when a chelant is a supplied as a mixture of closely related molecules having different molecular weights, then the average molecular weight of the material supplied should be used. For example, though phytic acid is often used to refer solely to inositol hexakisphosphate (IP6), commercial sources of phytic acid often comprise substantial amounts of inositol having lesser degrees of phosphorylation, such as IP2, IP3, IP4 and IP5. In this case, where the material supplied is a mixture it can be treated as a single material having an average degree of phosphorylation and the MW calculated accordingly. Suitable chelants herein include $C_2$-$C_6$ dicarboxylic and tricarboxylic acids, such as succinic acid, malic acid, tartaric acid and citric acid; $C_3$-$C_6$ monocarboxylic acids substituted with hydroxyl, such as gluconic acid; picolinic acid; amino acids such as glycine; phytic acid, salts thereof and mixtures thereof. Also suitable are tripolyphosphates. Longer chain linear polyphosphates, though good chelants, are susceptible to hydrolysis in aqueous compositions. Upon hydrolysis they form orthophosphates which form insoluble zinc complexes. Accordingly the amount of linear polyphosphates having an average chain length of four or more phosphate groups is kept to less than 0.2%, preferably less than 0.1%. Most preferably, these longer chain linear polyphosphates are not used as chelants.

Some materials, orthophosphate in particular, might be considered to be chelants in that they are bi- or multidentate ligands having at least two groups capable of binding to the divalent metal ions but nevertheless form insoluble zinc salts and are therefore not useful chelants for the present invention. A useful chelant or chelant mixture for the purpose of the present invention is one which provides for at least 80% of the zinc added to the composition being solubilised. A method for determining soluble zinc is set out below. Orthophosphates have often been used as buffers in oral compositions. However, since orthophosphate ions form tightly bound insoluble complexes with zinc the present composition preferably does not include them and, if they are present, the molar ratio of orthophosphate ions to zinc ions should be less than 0.2:1, preferably less than 0.1:1 and more preferably less than 0.05:1. The preferred chelants form water soluble zinc complexes on their own at pH 5.5, i.e. a neutral salt or complex of zinc ion with the chelant is soluble in water at a concentration of at least 1% at pH 5.5.

Phytate is a preferred chelant herein because it also provides stain removal benefits. However, because stannous phytate is not soluble it is preferably not used as the sole chelant and is preferably used in combination with the organic acids described in this section. As indicated above, commercial phytic acid often comprises substantial amounts of inositol having lesser degrees of phosphorylation than 6, such as IP2, IP3, IP4 and IP5. Unless specified otherwise herein 'phytic acid' or 'phytate' refers to inositol having an average degree of phosphorylation or more than 2, preferably at least 3, more preferably at least 4.

Organic acid chelants generally form soluble zinc complexes. Preferred organic acid chelants herein comprise citrate, malate, tartrate, gluconate, succinate, lactate, malonate, maleate, and mixtures thereof, whether added in their free acid or salt forms.

The molar ratio of the chelants used to divalent metal ions is at least 0.70:1, preferably at least 0.8:1 and can be as high as, say, 20:1. The molar ratio of chelants to divalent metal ions is the total number of moles of chelant(s) divided by the total number of moles of metal ions. Zinc citrate provides a chelant to zinc ratio of 2:3. Stannous gluconate provides a chelant to tin(II) ratio of 2:1. If an equimolar mixture of zinc citrate and stannous gluconate is used, the molar ratio of chelants to divalent metal ions is (2+2)/(3+1)=1:1. If each of stannous and zinc were provided as the citrate salt (ratio 2:3) then further free chelant would need to be added to provide a ratio of at least 0.70:1.

At the 5 to 6.5 pH range of the present composition, modelling work shows that most of the preferred chelants herein preferentially chelate the zinc ion, which is generally substantially solubilised within the oral composition as a chelated, though not necessarily neutral zinc species. In the compositions enumerated in the examples herein about 50% of the stannous ion is typically chelated. It has been found though that this is sufficient to give improved antimicrobial activity from the zinc/stannous combination without significant taste, staining or stability problems.

Total zinc and soluble zinc within oral compositions of the present invention can be measured using an atomic absorption method as follows.

Total zinc Weigh 1 g of composition into a 100 ml volumetric flask. Add 30 ml 3M hydrochloric acid to approximately half fill the flask, add a magnetic stirrer bar and stir for at least 60 mins to disperse the composition. Remove the stirrer bar and heat the solution in a boiling water bath for 60 mins. Cool the solution and dilute to volume with deionised water. Centrifuge the solution at 10000 rpm for 10 minutes. If the supernatant is not clear, further centrifuge it for 10 minutes. 2 ml of clear supernatant is diluted to 100 ml with 1M hydrochloric acid.

Soluble zinc Into a 50 ml centrifuge tube, weigh 3 g±0.01 g composition and 9 g±0.01 g 10% deionise water. Add 6 glass balls and cap. Vortex for 2 minutes, then centrifuge for 15 mins at 15000 rpm. Weigh 0.5 g supernatant into a 250 ml volumetric flask, add 30 ml 3M hydrochloric acid and dilute to volume with water. Dilute 5 ml of this solution to 10 ml with 1M hydrochloric acid.

Using reference solutions of 0.1, 0.2, 0.3, 0.5, 0.7 mg/L solutions of zinc in 1M hydrochloric acid the amount of zinc in each case (total and soluble) can be measured using an atomic absorption spectrometer (AAS) using 1M hydrochloric acid as a blank solution for auto-zeroing and AAS settings of:

| | |
|---|---|
| Wavelength | 213.9 nm |
| Gases used | Air/acetylene |
| Burner head | 10 cm |
| Slit width | 0.7 nm |
| Background correction | On |

In preferred compositions of the present invention the level of soluble zinc ion is in the range from 500 to 5000 ppm, preferably from 1000 to 4000 ppm.

Water

The term "orally acceptable carrier" as used means a liquid or semi-solid vehicle such as a paste or a gel for containing the active ingredients of the present invention and delivering them to the oral cavity. The carrier includes at least 20% total water. Water is commonly used as a carrier material in oral compositions. It is useful as a processing aid, is benign to the mouth and it assists in quick foaming of toothpastes. Water may be added as an ingredient in its own right or it may be present as a carrier in other common raw materials such as sorbitol and sodium lauryl sulphate. The term 'total water' as used herein means the total amount of water present in the composition, whether added separately or as a solvent or carrier for other raw materials but excluding that which may be present as water of crystallisation in certain inorganic salts. Preferred dentifrice compositions herein are aqueous compositions comprising from 20% to 65%, preferably from 30% to 55%, more preferably from 40% to 50% total water. The carrier can also include other conventional additives in oral care compositions such as desensitizing agents, teeth whitening agents such as peroxide sources, herbal agents, buffers, anti-staining agents, thickening materials, humectants, surfactants, a flavour system, sweetening agents, and colouring agents. The oral compositions herein are preferably single phase, by which is meant that all of the ingredients of the composition are containable within in a single compartment of a container and no further mixing is required before use.

The pH of the compositions herein is from 5 to 6.5, more preferably from 5.5 to 6.0. The pH of a dentifrice composition is measured from a 3:1 aqueous slurry of the dentifrice, i.e., 3 parts water to 1 part dentifrice.

Other Ingredients

The present oral composition can comprise the usual and conventional ancillary components as more fully described hereinafter.

An optional but preferred component of the compositions herein is a humectant. The humectant serves to keep the dentifrice from hardening upon exposure to air, to give a moist feel to the mouth, and, for particular humectants, to impart a desirable sweetness of flavour. The humectant, on a pure humectant basis, generally comprises from 5% to 70%, preferably from 15% to 45%, by weight of the composition. Suitable humectants include edible polyhydric alcohols such as glycerin, sorbitol, xylitol, butylene glycol, polyethylene glycol, and propylene glycol, especially sorbitol and glycerin. The compositions of the present invention will generally also include a surfactant. Useful surfactant types include anionic, nonionic, cationic and betaine surfactants. Anionic surfactants can be included to provide cleaning and foaming properties, and are typically used in an amount from 0.1% to 2.5%, preferably from 0.3% to 2.5% and most preferably from 0.5% to 2.0% by weight. Cationic surfactants can also be used though care needs to be taken over their compatibility with other ingredients. They would typically be used at levels similar to those of the additional anionic surfactants, as would betaine surfactants. Some nonionic surfactants may be useful at substantially higher levels, such as up to 20% if it is desired to use them to form a ringing gel.

Anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Also useful herein are sarcosinate surfactants, alkyl sulfoacetates, isethionate surfactants and taurate surfactants, such as lauroyl sarcosinate, myristoyl sarcosinate, palmitoyl sarcosinate, stearoyl sarcosinate and oleoyl sarcosinate. All of the foregoing are generally used as their alkali metal or ammonium salts.

Examples of suitable nonionic surfactants include the poloxamers, polyethylene oxide condensates of alkyl phenols, long chain tertiary amine oxides, long chain tertiary phosphine oxides, long chain dialkyl sulfoxides and mixtures of such materials. Preferred betaine surfactants include cocoamidoethyl betaine, cocoamidopropyl betaine, lauramidopropyl betaine and the like.

Cationic surfactants useful in the present invention include derivatives of aliphatic quaternary ammonium compounds having one long alkyl chain containing from 8 to 18 carbon atoms such as lauryl trimethylammonium chloride; cetyl pyridinium chloride; cetyl trimethylammonium bromide; di-isobutylphenoxyethyl-dimethylbenzylammonium chloride; cetyl pyridinium fluoride; etc. Some of these cationic surfactants are also useful as anti-microbial agents.

In preparing tooth pastes or gels, it is often necessary to add a thickening agent or binder to provide a desirable consistency of the composition, to provide desirable active release characteristics upon use, to provide shelf stability, and to provide stability of the composition, etc. Thickening agents can include carboxyvinyl polymers, carrageenan, nonionic cellulose derivatives such as hydroxyethyl cellulose (HEC), and water soluble salts of cellulose derivatives such as sodium carboxymethylcellulose (NaCMC). Natural gums such as gum karaya, xanthan gum, gum arabic, and gum tragacanth can also be used herein. Suitable thickening agent levels can range from 0.1 to 5%, and higher if necessary.

The present composition which contains stannous ions can be used to treat dental hypersivity, caused by uncovered dentin. Uncovered dentin makes the tubules vulnerable to a variety of stimuli which can induce pain. This is thought to be as a result of fluid movement within the dentinal tubules stimulating nerve fibres. The physical or chemical deposition of deposits into open dentinal tubuli is an accepted mechanism of action for effective treatment of hypersensitivity. Stannous salts have been shown to deposit into tubules from neat solutions and from simple formulations. Deposition may include reactivity with mineral, collagen or dentinal fluid. A key mechanism for stannous salts anti-hypersensitivity may be to actively block tubules through deposition mechanisms—either mineral or fluid.

Another optional component of the present composition is a further dentinal desensitizing agent to control hypersensitivity, especially salts of potassium and strontium such as potassium nitrate.

Organic antimicrobial agents may also be employed. Included among such agents are water insoluble non-cationic antimicrobial agents such as halogenated diphenyl ethers, particularly triclosan and essential oils such as thymol. Water soluble antimicrobials include quaternary ammonium salts such as cetyl pyridinium chloride. Enzymes are another type of active that may be used in the present compositions. Useful enzymes include those that belong to the category of proteases, lytic enzymes, plaque matrix inhibitors and oxidases. The oxidases also have whitening/cleaning activity, in addition to anti-microbial properties. Such agents are disclosed in U.S. Pat. Nos. 2,946,725, and 4,051,234.

Flavouring and sweetening agents are preferably also included in the present composition. Suitable flavouring agents and sweetening agents are well known in the art. Suitable flavour levels in the present oral compositions herein are from 0.1% to 5.0%, more preferably from 0.5% to 1.5%, by weight. Typically, a flavour oil will be manufactured in a separate step and will comprise multiple components, natural and/or synthetic in origin, in order to provide a balanced flavour which is acceptable to a broad range of people. Flavour components can be selected from mint, spice, fruit, citrus, herbal, medicinal, and common food flavour types (e.g. chocolate). Illustrative, but non-limiting examples of such components include hydrocarbons such as limonene, caryophyllene, myrcene, and humulene; alcohols such as menthol, linalool, 3-decanol, and pinocarveol; ketones such as piperitone, menthone, spicatone, and l-carvone; aldehydes such as acetaldehyde, 3-hexanal, or n-octanal; oxides such as menthofuran, piperitone oxide, or carvyl acetate-7,7 oxide; acids such as acetic and ocenoic; and sulphides such as dimethyl sulphide. Components also include esters such as menthyl acetate, benzyl isobutyrate, and 3-octyl acetate. The flavour components may also include essential oils such as peppermint oils from e.g., *Mentha piperita* and *Mentha arvensis*; spearmint oils such as those from *Mentha cardiaca* and *Mentha spicata*; sage oil, parsley oil, marjoram oil, *cassia* oil, clove bud oil, cinnamon oil, orange oil, lime oil, eucalyptus oil and anise oil. Other suitable components are cinnamic aldehyde, eugenol, ionone, anethole, eucalyptol, thymol, methyl salicylate, vanillin, ethyl vanillin, and vanilla extracts. Flavour components are described in more detail in Fenaroli's Handbook of Flavor Ingredients, Third Edition, Volumes 1 & 2, CRC Press, Inc. (1995), and Steffen Arctander's Perfume and Flavour Chemicals, Volumes 1 & 2, (1969). A physiological cooling agent can also be incorporated into the flavour oil. The coolant can be any of a wide variety of materials. Included among such materials are carboxamides, menthol, acetals, ketals, diols, and mixtures thereof. Preferred coolants herein include the p-menthane carboxamide agents such as N-ethyl-p-menthane-3-carboxamide, (known commercially as "WS-3") and mixtures thereof and menthone glycerine acetal (known commercially as "MGA"). Further coolants suitable for the present invention are disclosed in WO 97/06695.

The compositions herein can further include herbal ingredients such as extracts of chamomile, oak bark, melissa, rosemary and salvia. These, and some of the herb-derived flavouring components mentioned above (such as thymol) can be included at levels just sufficient to provide a contribution to the flavour or they can be added at higher levels, such as 1% or more, in order to provide a greater therapeutic effect.

Sweetening agents which can be used include sucrose, glucose, saccharin, sucralose, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate, sucralose and sodium saccharin, and mixtures thereof. A composition preferably contains from 0.1% to 3% of these agents, more preferably from 0.1% to 1%.

The compositions may further include usual pigments, dyes and opacifiers, such as titanium dioxide. It will be appreciated that selected components for the compositions must be chemically and physically compatible with one another.

EXAMPLES

The following examples further describe and demonstrate toothpaste embodiments within the scope of the present invention. These examples are given solely for the purpose of illustration and are not to be construed as limitations of the present invention as many variations thereof are possible.

Toothpaste compositions according to the present invention are shown below with amounts of components in weight %. These compositions are made using conventional methods.

| Ingredient | A | B | C | D | E | F | G | H |
|---|---|---|---|---|---|---|---|---|
| Sorbitol sol. (70%) | 40.37 | 40.57 | 41.63 | 40.50 | 40.57 | 40.57 | 40.57 | 40.57 |
| Phytic acid (50% soln) | 0.800 | 0.800 | 0.800 |  | 0.800 | 0.800 | 0.800 | 0.800 |
| Zinc citrate | 0.955 | 0.533 | 0.533 | 0.788 | 0.533 |  | 0.533 | 0.533 |
| Zinc lactate |  |  |  |  |  | 0.736 |  |  |
| Potassium nitrate |  |  |  |  |  |  |  | 5.00 |
| Stannous fluoride |  |  |  |  | 0.454 |  |  |  |
| Sodium fluoride | 0.243 | 0.243 | 0.243 | 0.243 |  | 0.243 | 0.243 | 0.243 |
| Sodium gluconate | 1.064 | 1.064 | 0.699 |  | 1.064 | 1.064 | 0.675 | 1.064 |
| Stannous chloride | 1.16 | 1.16 | 0.762 | 0.209 |  |  | 1.16 | 1.16 |
| HEC | 0.30 | 0.30 | 0.30 | 0.30 | 0.30 | 0.30 | 0.30 | 0.30 |
| Na Citrate |  |  |  | 0.27 |  |  |  |  |
| Na CMC | 1.30 | 1.30 | 1.30 | 1.30 | 1.30 | 1.30 | 1.30 | 1.30 |
| Carrageenan | 0.70 | 0.70 | 0.70 | 0.70 | 0.50 | 0.50 | 0.70 | 0.70 |
| Silica abrasive | 12.50 | 12.50 | 12.50 | 17.00 | 12.50 | 12.50 | 12.50 | 12.50 |
| $TiO_2$ (Anatase) | 0.53 | 0.53 | 0.53 | 0.53 | 0.53 | 0.53 | 0.53 | 0.53 |
| SLS (28% soln.) | 5.00 | 5.00 | 5.00 | 5.00 | 5.00 | 5.00 | 5.00 | 5.00 |
| Na Saccharin | 0.30 | 0.30 | 0.30 | 0.30 | 0.30 | 0.30 | 0.30 | 0.30 |
| Flavor | 1.10 | 1.10 | 1.10 | 1.00 | 1.10 | 1.10 | 1.10 | 1.10 |
| NaOH 50% | 1.00 | 0.95 | 0.84 |  | 0.80 | 0.90 | 0.90 | 1.10 |
| Water and minors, e.g., color soln. | qs | qs | qs | qs | qs | qs | qs | qs |
| Total water | 48.29 | 48.60 | 48.78 | 47.53 | 49.78 | 49.79 | 48.99 | 43.60 |
| Target pH | 5.8 | 5.8 | 5.8 | 5.8 | 5.8 | 5.8 | 5.8 | 6.0 |
| Total metal ions (mmol %) | 98.10 | 77.60 | 59.97 | 47.99 | 77.60 | 60.10 | 77.60 | 77.60 |
| Total chelant ions (mmol %) | 85.96 | 72.30 | 55.57 | 35.14 | 72.30 | 90.77 | 54.47 | 72.30 |
| Ratio Chelant:metal | 0.88 | 0.93 | 0.93 | 0.73 | 0.93 | 1.51 | 0.70 | 0.93 |
| % Soluble Zn | 84 | 80 | 81 | 97 | na | na | na | na |
| % Difference vs. Crest ® Cavity Protection[1] (NaF)* | 26 | 21 | 17 | 10 | na | na | na | na |

[1]Crest ® Cavity Protection is a formulation marketed in the US that does not contain stannous or zinc ions.
*Whole mouth average average score.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition or a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An aqueous oral composition comprising:
 a single phase comprising:
 a) from about 0.2% to about 3% divalent metal ions comprising:
  (i) from about 0.1% to about 1.5% of zinc ions;
  (ii) from about 0.1% to about 2% of tin (II) ions; and
 b) a source of fluoride ions;
 c) a silica dental abrasive;
 d) one or more chelants having a MW of less than about 1000, wherein the chelants comprise less than about 0.2% linear polyphosphates having a chain length of four or more;
 e) an orally acceptable carrier comprising at least about 20% total water;
 wherein the pH of the composition is from about 5 to about 6.5, the molar ratio of the chelants to the divalent metal ions is at least about 0.70:1 and at least about 80% by weight of the total zinc ions are solubilised within the composition and wherein, if orthophosphate ions are present, the molar ration of orthophosphate ions to zinc ions is less than about 0.2:1.

2. An oral composition according to claim 1 having a pH in the range from about 5.5 to about 6.5.

3. An oral composition according to claim 1 wherein the chelants are selected from $C_2$-$C_6$ dicarboxylic and tricarboxylic acids; $C_3$-$C_6$ monocarboxylic acids substituted with hydroxyl, picolinic acid, amino acids, phytic acid, salts thereof and mixtures thereof.

4. An oral composition according to claim 3 wherein the chelants comprise phytate.

5. An oral composition according to claim 3 wherein the chelants comprise citrate, malate, tartrate, gluconate, succinate, lactate, malonate, maleate, or mixtures thereof.

6. An oral composition according to claim 1 wherein the fluoride ions are provided by sodium fluoride, potassium fluoride, stannous fluoride or mixtures thereof.

7. An oral composition according to claim 1 wherein the tin (II) ions are provided by stannous chloride, stannous fluoride, stannous gluconate or mixtures thereof.

8. An oral composition according to claim 1 wherein the zinc ions are provided by zinc citrate, zinc gluconate, zinc lactate or mixtures thereof.

9. An oral composition according to claim 1 wherein the molar ratio of stannous ions to zinc ions is from about 0.5:1 to about 3:1.

10. Method for the treatment of dental hypersensitivity comprising treating teeth with an oral composition comprising:
a single phase comprising:
  a) from about 0.2% to about 3% divalent metal ions comprising:
    (i) from about 0.1% to about 1.5% of zinc ions;
    (ii) from about 0.1% to about 2% of tin (II) ions; and
  b) a source of fluoride ions;
  c) a silica dental abrasive;
  d) one or more chelants having a MW of less than about 1000, wherein the chelants comprise less than about 0.2% linear polyphosphates having a chain length of four or more;
  e) an orally acceptable carrier comprising at least about 20% total water;
wherein the pH of the composition is from about 5 to about 6.5, the molar ratio of the chelants to the divalent metal ions is at least about 0.70:1 and at least about 80% by weight of the total zinc ions are solubilised within the composition and wherein, if orthophosphate ions are present, the molar ratio of orthophosphate ions to zinc ions is less than about 0.2:1.

11. An aqueous oral composition comprising:
a single phase comprising:
  a) from about 0.4% to about 1.5% divalent metal ions comprising:
    (i) from about 0.15% to about 0.5% of zinc ions;
    (ii) from about 0.2% to about 0.7% of tin (II) ions; and
  b) from about 0.01% to about 0.35% fluoride ions;
  c) from about 6% to about 50% of a dental abrasive
  d) phytic acid and an organic acid chelant selected from succinic acid, malic acid, tartaric acid, citric acid, gluconic acid, picolinic acid, or glycine, or salts thereof and mixtures thereof;
  e) an orally acceptable carrier comprising at least about 20% total water;
wherein the pH of the composition is from about 5.5 to about 6.5, the molar ratio of the chelants to the divalent metal ions is at least about 0.8:1, at least about 90% by weight of the total zinc ions are solubilised within the composition and wherein, if orthophosphate ions are present, the molar ration of orthophosphate ions to zinc ions is less than about 0.2:1.

12. An oral composition according to claim 11 wherein the dental abrasive is a silica dental abrasive with an average particle size of from about 5 μm to about 15 μm.

13. An oral composition according to claim 11 wherein the composition further comprises from about 15% to about 45% of a humectant.

14. An oral composition according to claim 11 wherein the composition further comprises from about 0.5% to about 2% of a surfactant.

15. An oral composition according to claim 11 wherein the composition further comprises from about 0.1% to about 5% of a thickening agent.

16. An oral composition according to claim 11 wherein the composition further comprises from about 0.5% to about 1.5% of a flavouring agent.

17. An oral composition according to claim 11 wherein the composition further comprises from about 0.1% to about 1% of a sweetener.

18. An aqueous oral composition comprising:
a single phase comprising:
  a) from about 0.4% to about 1.5% divalent metal ions comprising:
    (i) from about 0.15% to about 0.5% of zinc ions;
    (ii) from about 0.2% to about 0.7% of tin (II) ions; and
  b) from about 0.01% to about 0.35% fluoride ions;
  c) from about 6% to about 50% of a silica dental abrasive with an average particle size of from about 5 μm to about 15 μm;
  d) one or more chelants having a MW of less than about 1000, wherein the chelants comprise less than about 0.2% linear polyphosphates having a chain length of four or more;
  e) an orally acceptable carrier comprising at least about 20% total water;
wherein the pH of the composition is from about 5.5 to about 6.5, the molar ratio of the chelants to the divalent metal ions is at least about 0.8:1, at least about 90% by weight of the total zinc ions are solubilised within the composition and wherein, if orthophosphate ions are present, the molar ratio of orthophosphate ions to zinc ions is less than about 0.2:1.

* * * * *